(12) United States Patent
Shire et al.

(10) Patent No.: US 10,967,172 B1
(45) Date of Patent: Apr. 6, 2021

(54) METHOD AND APPARATUS FOR MINIMALLY-INVASIVE IMPLANTATION OF ELECTRODES AND FLEXIBLE, THIN-FILM SUBSTRATES INTO CORTICAL OR SUB-CORTICAL STRUCTURES OF THE BRAIN

(71) Applicants: Douglas B Shire, Ithaca, NY (US); Lauren N Ayton, Ithaca, NY (US); Patricia I Wong, Ithaca, NY (US); Marcus D Gingerich, Newfield, NY (US)

(72) Inventors: Douglas B Shire, Ithaca, NY (US); Lauren N Ayton, Ithaca, NY (US); Patricia I Wong, Ithaca, NY (US); Marcus D Gingerich, Newfield, NY (US)

(73) Assignee: Bionic Eye Technologies, Inc., Ithaca, NY (US)

( * ) Notice: Subject to any disclaimer, the term of this patent is extended or adjusted under 35 U.S.C. 154(b) by 54 days.

(21) Appl. No.: 16/234,151

(22) Filed: Dec. 27, 2018

Related U.S. Application Data

(60) Provisional application No. 62/610,635, filed on Dec. 27, 2018.

(51) Int. Cl.
| | | |
|---|---|---|
| *A61N 1/36* | (2006.01) | |
| *A61B 17/34* | (2006.01) | |
| *A61N 1/05* | (2006.01) | |
| *A61N 1/375* | (2006.01) | |
| *A61N 1/372* | (2006.01) | |

(52) U.S. Cl.
CPC ........ *A61N 1/0534* (2013.01); *A61B 17/3468* (2013.01); *A61N 1/36125* (2013.01); *A61N 1/37205* (2013.01); *A61N 1/37514* (2017.08)

(58) Field of Classification Search
CPC .............. A61N 1/0534; A61N 1/37514; A61N 1/36125; A61N 1/37205; A61B 17/3468
See application file for complete search history.

(56) References Cited

U.S. PATENT DOCUMENTS

| | | |
|---|---|---|
| 5,823,941 A | 10/1998 | Shaunnessey |
| 6,011,996 A | 1/2000 | Gielen et al. |
| 8,396,561 B2 | 3/2013 | Pezaris et al. |
| 9,107,515 B2 | 8/2015 | Boularot et al. |
| 9,216,015 B2 | 12/2015 | Wilson |
| 9,247,895 B2 | 2/2016 | Venkatesan et al. |
| 9,386,974 B2 | 7/2016 | Wilson |
| 9,604,060 B2 | 3/2017 | Burchiel et al. |
| 2004/0002635 A1 | 1/2004 | Hargrove et al. |
| 2007/0106143 A1 | 5/2007 | Flaherty |
| 2009/0124965 A1* | 5/2009 | Greenberg ........... A61N 1/0539 604/67 |
| 2010/0198297 A1 | 8/2010 | Cogan et al. |
| 2014/0148729 A1 | 5/2014 | Schmitz et al. |
| 2015/0045642 A1 | 2/2015 | Cogan et al. |
| 2017/0113048 A1 | 4/2017 | Giftakis et al. |
| 2018/0093099 A1 | 4/2018 | Cogan et al. |

FOREIGN PATENT DOCUMENTS

GB  PCT/GB02/00851 A1  9/2002

* cited by examiner

*Primary Examiner* — George Manuel
(74) *Attorney, Agent, or Firm* — Randall L. Reed; Millen Mayer LLP

(57) ABSTRACT

An apparatus for implanting electrodes in neural tissue to connect a neural modulator to the tissue to send and receive signals from the neural tissue and a method for implanting the electrodes.

26 Claims, 20 Drawing Sheets

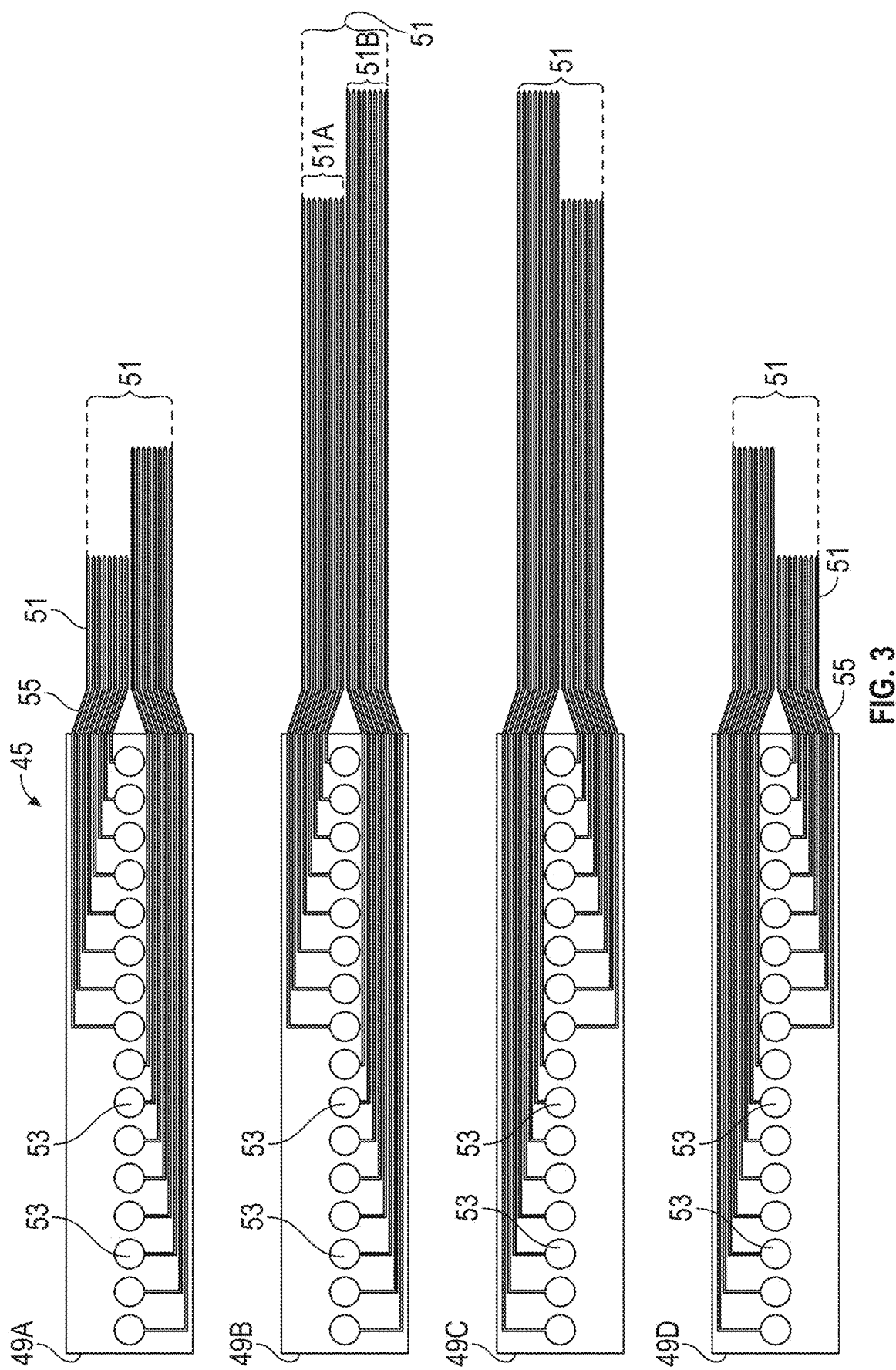

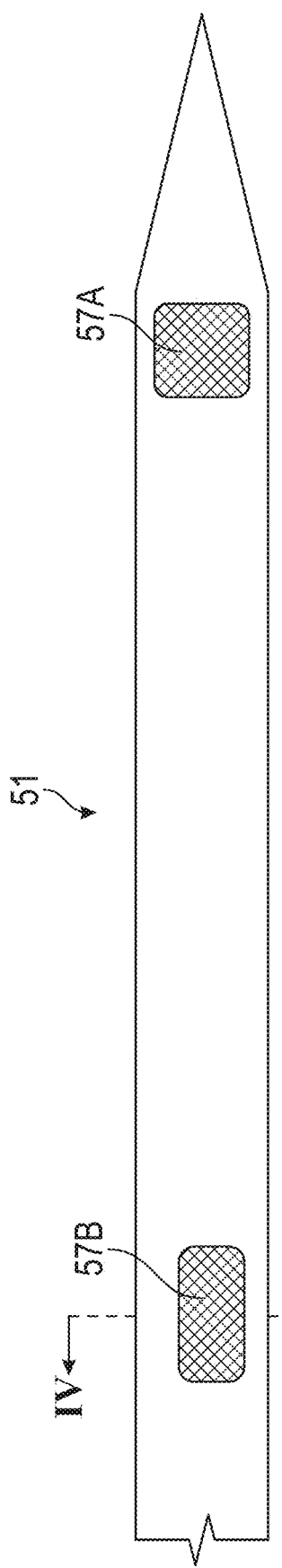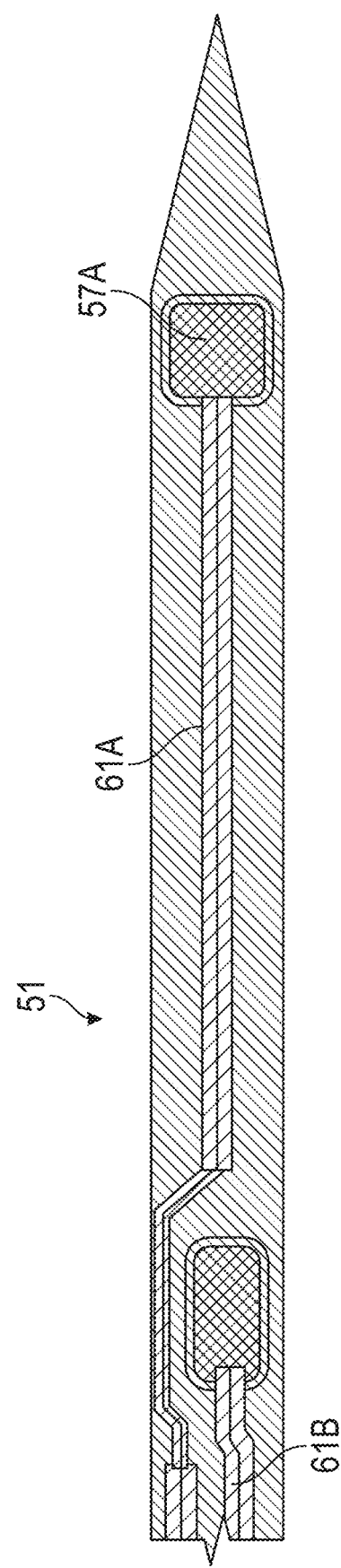

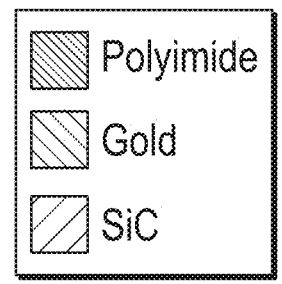
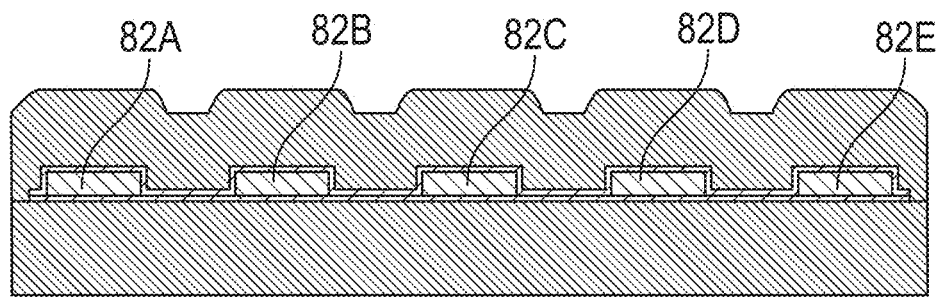
FIG. 6
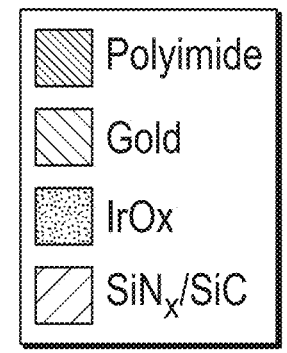
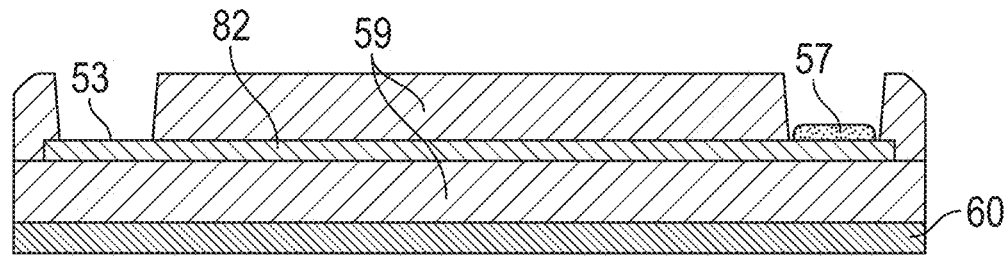
FIG. 6A

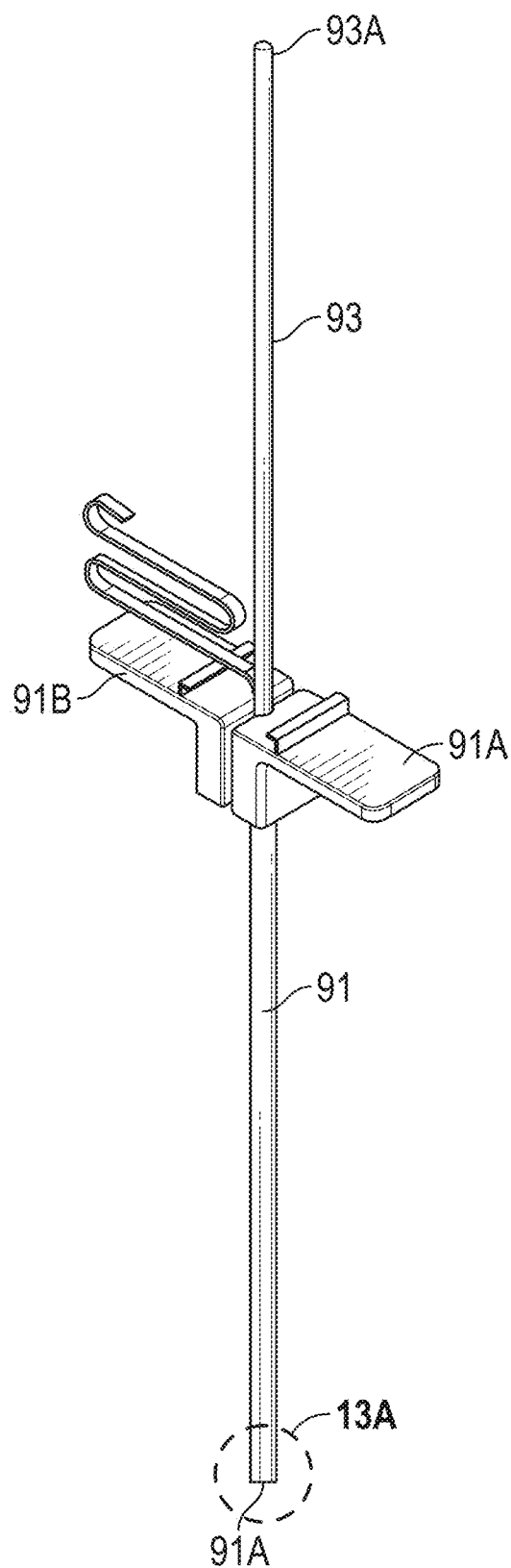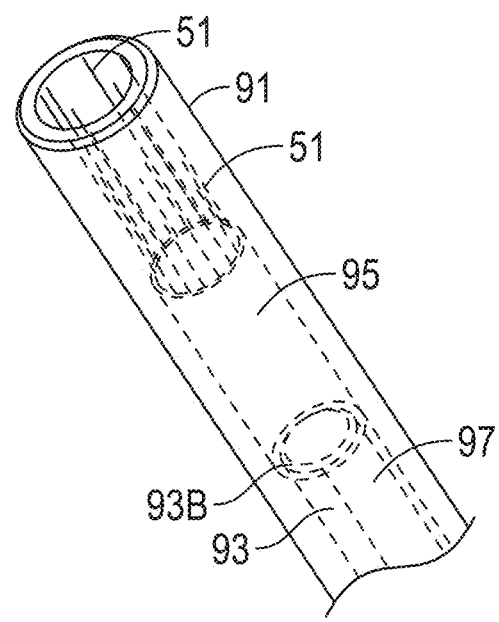
FIG. 13A
FIG. 13

```
201
```
Scanning and mapping the brain to determine the desired insertion depth for the target organ or tissue (LGN)

```
202
```
Form an electrode array - ribbon cable assembly and place inside a split sheath inserter with the distal end of the electrode array with tines completely inside the end of the inserter

```
203
```
Position an insertion rod in the split sheath inserter with the narrow distal end positioned at the back of the electrode array and the proximal end extending out of the split sheath inserter

```
204
```
Perform a craniotomy in the skull of the subject at a point above the target tissue (e.g.,LGN) into which the electrode array will be inserted

```
205
```
Insert the loaded split sheath inserter into the brain coarsely towards the target tissue to the predetermined depth

```
206
```
When the tip of the loaded split sheath inserter reaches the outer edge of the target tissue, stop coarse insertion of the split sheath inserter

```
207
```
Using a hydraulic micro-drive attached to the insertion rod, push the tines of the array slowly out of the split sheath inserter so that it penetrates the target tissue to the desired depth

```
208
```
Remove the split sheath inserter in the standard manner by parting the opposing 'handles'

```
209
```
Affix the previously-connected packaged stimulator to the end of the ribbon cable in the opening previously made in the skull

FIG. 16

METHOD AND APPARATUS FOR MINIMALLY-INVASIVE IMPLANTATION OF ELECTRODES AND FLEXIBLE, THIN-FILM SUBSTRATES INTO CORTICAL OR SUB-CORTICAL STRUCTURES OF THE BRAIN

CROSS-REFERENCE TO RELATED APPLICATIONS

This application claims the benefit of priority under applicable US laws of U.S. Provisional Application Ser. No. 62/610,635 filed on Dec. 27, 2017 the content of which is relied upon and incorporated herein by reference in its entirety.

FIELD OF INVENTION

The present invention relates to a system and method for implanting electrodes in living tissue, more specifically to implanting electrodes in brain tissue.

BACKGROUND OF INVENTION

Medical science for some time has been developing various ways to stimulate living tissue for a variety of purposes. Among these are restoring the ability of a paralyzed person to control and move their limbs, as well as for restoration of sight. Deep brain stimulation (DBS), an example of this effort, is a rapidly growing medical field, which is used for a number of movement disorders (such as Parkinson's disease), seizure disorders (e.g. epilepsy), chronic pain, mood disorders, neurological and psychiatric conditions. In DBS, electrodes are placed in the brain, somewhere below the cortex, in either white matter fiber tracts or nuclei in the brain, and are used to stimulate specific regions for the alleviation of symptoms. In addition, the electrodes used for DBS also can be used to stimulate cortical neurons or to record cortical signals, often in conjunction with implanted stimulating systems.

The implantation of electrodes, DBS or otherwise, creates a brain-machine interface (BMI). For example, electrode arrays implanted into the motor regions of the cortex could utilize signals generated by a patient thinking about a physical movement, and convert this to an electrical signal to stimulate the motor cortex and initiate that movement. The potential for such thought-invoked control signals is significant.

One of the main challenges in the field has been the development of electrodes (and stimulation paradigms) that can selectively activate specific neurons or neuronal pathways. For example, a recent study has shown that the DBS electrode location was highly correlated with clinical improvement in Parkinson's patients, with structural connectivity to the supplementary motor cortex linked to a positive outcome, whilst functional connectivity to the primary motor cortex led to worse outcomes. In addition, ≈70% of the cortical neurons lie below the surface, and so surface electrodes are not able to effectively activate the deeper layers. For example, work by the NIH found that surface electrodes placed onto the occipital lobe produced much lower spatial resolution and required 100× greater charge to reach stimulation threshold vs. penetrating microelectrodes placed into the occipital cortex. It is clear that superficial diffuse electrical stimulation does not provide optimal patient benefit, and hence our invention aims to address this issue via smaller electrodes that are microfabricated within novel flexible arrays, which because of their small size and flexible mechanical properties can be passed into neural tissue (e.g., cortical or subcortical structures) with minimal damage. This invention also describes the means to deploy our ultra-thin microfabricated electrode arrays that are connected to local or external neuromodulation circuits; the arrays require special techniques and tools for surgical implantation because of their flexible nature. The small size of our microfabricated electrodes enhances the ability to selectively stimulate target nerve cells or nerve pathways, which should enhance the clinical benefits for patients.

BRIEF SUMMARY OF THE INVENTION

The present inventions to solve the problems discussed provides a system for modulating neural tissue in a mammal having: a) an implantable neural modulator; b) an electrode array of micro-fabricated ultrathin tines; c) a micro-fabricated communication bus with insulated signal lines connecting the set of tines to the neural modulator; d) wherein the tines are elongated in shape for insertion into living tissue with an electrically insulated exterior with the exception of at least one electrode on an exterior of each tine of the tines, the electrodes being individually connected by a separate insulated signal line of the communication bus to the stimulator; and e) wherein the set of tines are of varying length so the at least one electrode on each of the tines of the set of tines is positioned at varying depths in tissue as the set of tines are implanted in a target tissue. In a further aspect of the system the electrode array and ribbon connector can consist of a ribbon connector and electrode array micro-fabricated as two separate devices and then joined, or the ribbon connector and electrode array can be micro-fabricated as one unitary device.

In a further aspect of the system a spatial distribution of the tines in the target tissue is determined by fabrication parameters of the tines, the fabrication parameters being control of a net tensile or compressive stress of the material that the tines are fabricated from during a micro-fabrication process. In yet another aspect of the system there is at least one electrode on a tine is at a plurality of electrodes with each the electrode having its own separate insulated signal line in the communication buss. In yet another aspect of the system a tine of the set of tines can be up to 4 mm long and 2 to 10 microns in diameter. In yet a further aspect the mammal is a human and the target tissue is at least one of the LGN's of the human. In still another aspect the neural modulator is placed at the edge of the human's brain and the ribbon connector runs from the neural modulator to the electrode array to thereby communicatively connect them with a source of stimulating signals and also receive neural signals from the LGN. In yet another aspect the source of stimulating signals is a signal from a camera.

In a further aspect the shape of the elongated shaped tines is selected from a group consisting tines that are cylindrical in shape, spike shaped, and flat shaped. In yet another aspect of the system the electrode is configured in a manner selected from a group consisting of an electrode outer surface coplanar with the surface of the tine, and an electrode outer surface projecting out from the tine surface from 1 to 30 microns. In yet another aspect the system includes a signal processor incorporated into to the electrode array to process received signals generated by the target tissue, amplify them and retransmit them to the neural modulator, or to distribute received stimulus signals on a channel to one of a plurality of nearby electrodes.

In another aspect of the invention, it provides a method for implanting an electrode array into target brain tissue of a mammal having the steps of: a) encasing an electrode array with an attached ribbon connector in a split sheath inserter, such that the end of the electrode array with tines is retracted slightly from the front tip of the split sheath inserter and does not extend out of the front end, and the ribbon cable extends out of the back end of the split sheath inserter; b) positioning a first end of an insertion rod at a back end of the electrode array and having a second end extending up and out of the end of the split sheath inserter; c) Performing a craniotomy in the subject into which the electrode array will be embedded, the hole being cut at a position in the skull to allow insertion of the split sheath inserter to the outside surface of the tissue to be targeted; d) positioning the split sheath inserter for insertion into the brain of the subject through the hole cut in the skull; e) inserting the split sheath inserter with electrode array, ribbon connector and insertion rod encased in the split sheath inserter at a preset coarse rate until the leading end of the split sheath inserter contacts the outer surface of the target tissue, with navigation guidance e.g. through the brain provided by existing neurosurgical imaging tools; f) holding the split sheath inserter still and slowly and precisely inserting the tines at the end of the electrode array into the target tissue by pushing on the back of the electrode array with an insertion rod that is compatible with and connected to existing neurosurgical apparatus (e.g., a hydraulic micro-drive) until the tines are fully embedded in the target tissue, the insertion being informed by recording and monitoring neural activity and/or by stimulating target neural tissue to assess the response, behavior, or perception of the subject; g) withdrawing the split sheath inserter and insertion rod; and h) positioning the attached stimulator on the skull at the site of the craniotomy.

In a further aspect of the method the mammal is a human and the target tissue is the LGN. In yet another aspect of the method it includes an initial step of a scanning or imaging the target tissue prior to the step of inserting the split sheath inserter with electrode array and ribbon connector to thereby precisely locate the position of the target tissue to insert the tines into; alternatively, such mapping of the target tissue may be accomplished by probing and stimulating with microprobes at varied positions and depths.

In another variation of the invention it provides an electrical connection device for connecting a medical device to living neural tissue having: a) a ribbon connector with a first end for connecting to a medical device and a tine assembly at a second end for insertion into a target tissue; b) the tine assembly has a plurality of tines for insertion into the target tissue and each tine of the plurality of tines has an electrically insulated exterior with the exception of at least one electrode on it's surface the electrode being connected by an individual insulated line through the ribbon connector to the first end of the ribbon connector; c) the plurality of tines are of different lengths to thereby place the at least one electrode on each of the tine of the plurality of tines at different depths of the target tissue; and d) wherein each individual electrode with the individual insulated line can transmit a separate signal or receive a separate signal from the target tissue.

In another aspect of this variation of the invention the neural modulator can be connected to the first end of the electrical connection device and thereby transmit or receive signals on each of the individually insulated lines to each of the electrodes in the target tissue. In yet another aspect of the invention, the electrical connection device leads to a plurality of electrodes on a tine, each with a separate insulated line to the connector at the first end. In yet another aspect, the at least one electrode on a tine is a plurality of electrodes on the tine, and wherein at least two electrodes of the plurality of electrodes share an insulated line to the first end of the ribbon connector. In yet another aspect of the tine, the assembly includes signal processing circuits to process signals received by the electrode from the target tissue for transmission to the first end of the ribbon connector for reception by a medical device attached to the first end. In yet another aspect of the invention the neural modulator processes signals received from the target tissue to adjust the signals it then transmits to the target tissue over the connected insulated lines to the tines and thence to the electrodes thereon.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

FIG. 3 is a magnified view of the electrode array laid out flat;

FIG. 4 is a substantially magnified view of a tines;

FIG. 4A is a schematic diagram of the interior wiring of the tine depicted in FIG. 4;

FIG. 6 is a schematic diagram of a cross section of five lines that run from the electrode array through the ribbon connector to the stimulator/receiver within a neural modulator;

FIG. 6A is a schematic diagram of an exposed view, for illustration, of an embodiment of a typical conductive line running from an electrode in a tine to a bonding bump;

FIG. 13 is a view of the electrode array-ribbon connector positioned inside the split sheath inserter ready for insertion into the patient;

FIG. 13A is a close up outline view of the end of the split sheath inserter with the electrode array-ribbon connector and insertion rod as they would be positioned for initial insertion into the patient;

FIG. 16 is a flow chart of the steps of the method for inserting the electrode array-ribbon connector into the target organ or tissue of the patient.

DETAILED DESCRIPTION

I. Overview

U.S. Pat. No. 8,396,561 titled "A Visual Prosthesis and Method of Creating Visual Perception" of Pezaris et al., which is incorporated herein by reference, discloses a method for providing a mammal with visual information from an artificial source. This approach implants electrodes into the lateral geniculate nucleus (LGN), which is a structure along the visual pathway from the eye to the brain.

As noted, the present invention relates to electrodes implantable in living tissue and methods for implanting them in living tissue. Although the embodiment described in detail herein provides an example of an electrode array for implanting in brain tissue, specifically, laminar lateral geniculate nucleus (LGN) neural tissue, once those skilled understand all of the particulars of the invention or inventions described herein they will understand the applicability of the invention to other situations where tissue or nerve cells can be stimulated to rehabilitate, activate or restore the functioning of an organ, appendage, or part of a living human animal, etc. Such situations may for example use of the arrays to modulate the activity of other laminar neural tissue structures.

Figure 1C:
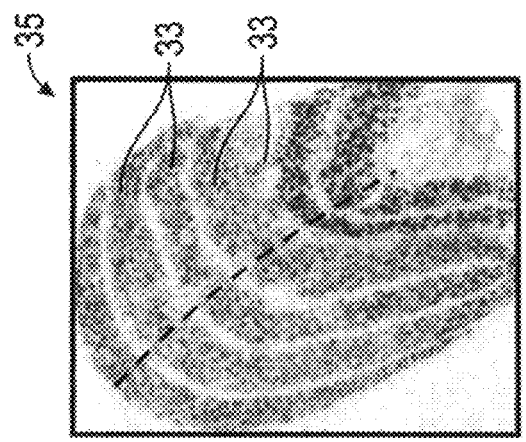
FIG. 1C is a close up of the cross section of the LGN depicted in FIG. 15.
Figure 1B:
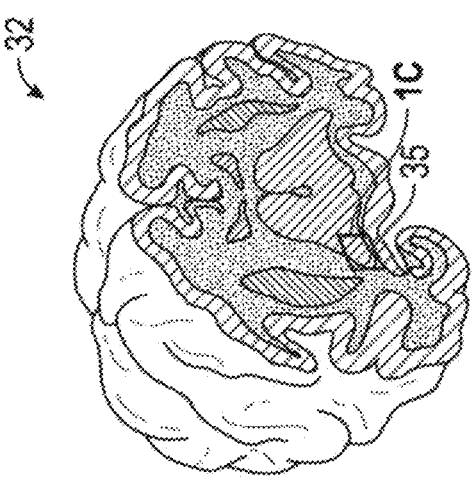
FIG. 1B is a cross sectional view of a human brain cut along line I-I in FIG. 1A.
Figure 1A:
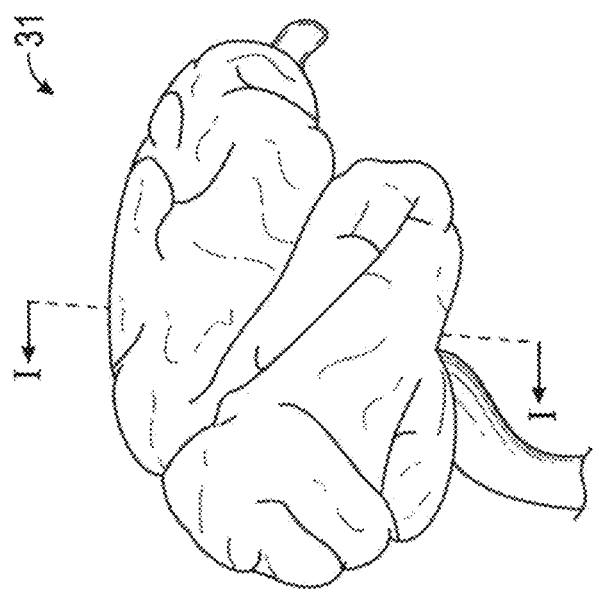
FIG. 1A is a side view of a human brain.

FIG. 1A provides a side view of a human brain 31. FIG. 1B is a cross sectional view of a human brain cut along line I-I of FIG. 1A. FIG. 1C is a closeup view of the cross section of the LGN 35 depicted in FIG. 1B. The different layers 37 of the LGN can be seen in FIG. 1C. The following is a description of a system and method implantable in the brain, e.g. for stimulating the LGN to restore vision, but applicable to other medical devices that also act upon the central nervous system.

II. Electrode Array and Connector Structure

Figure 2A:
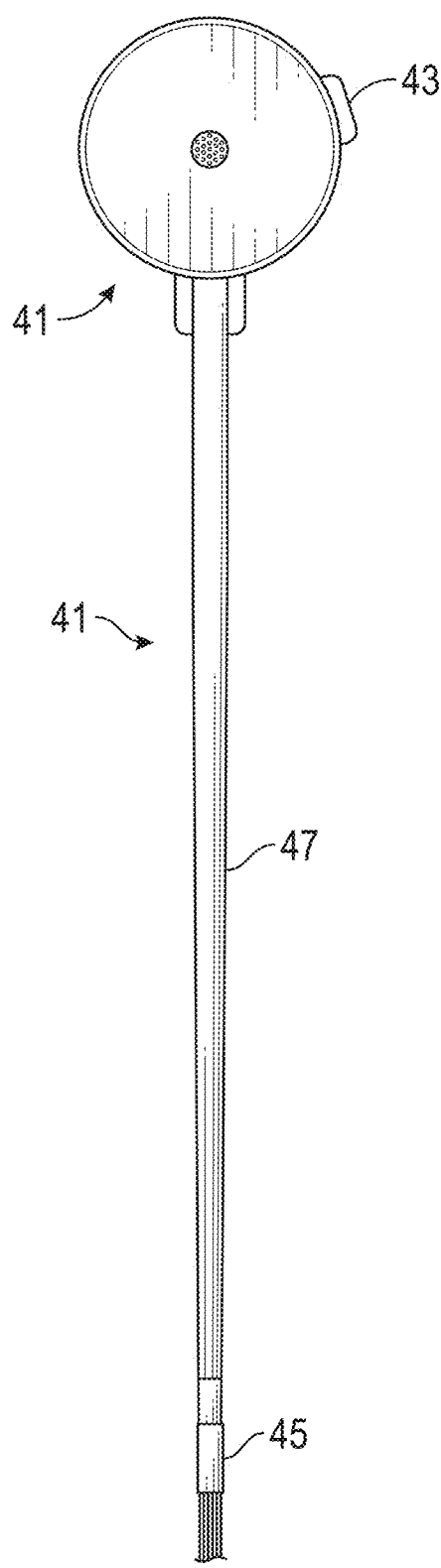
FIG. 2A is a plan view of the electrode assembly of the present invention.

FIG. 2A is a plan view of the electrode assembly of the present invention. The electrode assembly 41 consists of an implantable, wirelessly powered neural modulator 43, an electrode array 45, and a ribbon connector 47. Ribbon connector 47 electronically connects electrode array 45 to stimulator 43. As will be explained in detail below, installation of electrode assembly 41 in an animal or human consists of placing stimulator 43 on the surface of the brain of the recipient, with electrode array 45 inserted e.g. into the LGN of the patient. Ribbon connector 47 passes through the brain of the patient from modulator 43 to electrode array 45, so that they form electrical connections. Modulator 43 can be in communication with another external electronic device which provides stimulus and other commands to the implanted unit. Such stimulus commands could, for example, represent patterns which correspond spatially to the brightness of objects in the user's environment, as captured by a camera or visual input device. The video or visual input device, if employed, may be partially incorporated into a pair of glasses that may be worn by the user. Once the modulator 43 receives input e.g. from a video device mounted on glasses, it transmits a signal or signals electronically through the ribbon connector 47 to electrode array 45. In turn, electrode array 45 stimulates the LGN (or other tissue in the central nervous system) to e.g. provide visual information, or images, that the user will perceive, thus restoring some of the patient's sight. The neural modulator can have a number of functions; it can act as a neural stimulator, provide neural recording capability, and/or can process received neural signals to optimize the signals that will in turn be provided to the target neural tissue that the electrode array is implanted in.

Figure 2B:
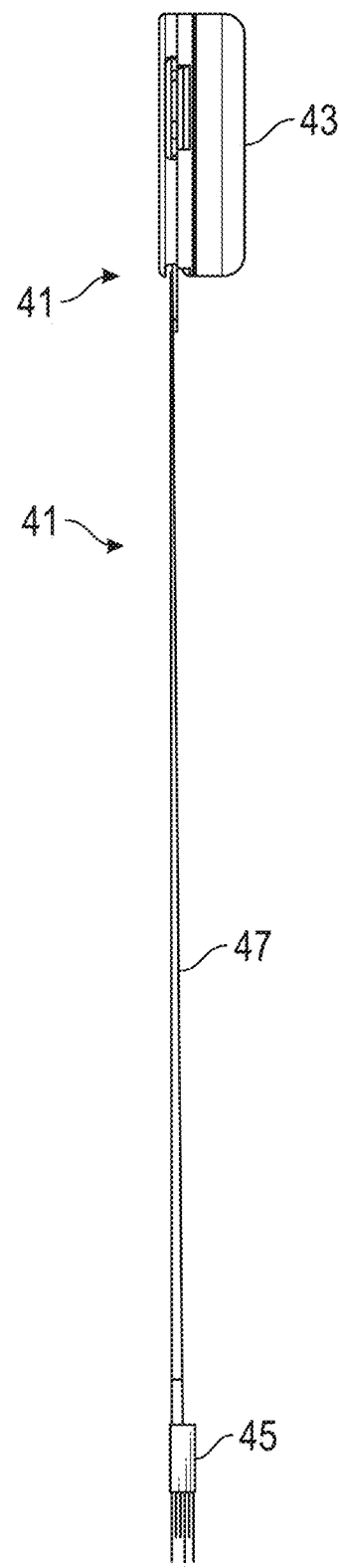
FIG. 2B is another plan view of the electrode assembly 41 of the present invention from the side.
Figure 2C:
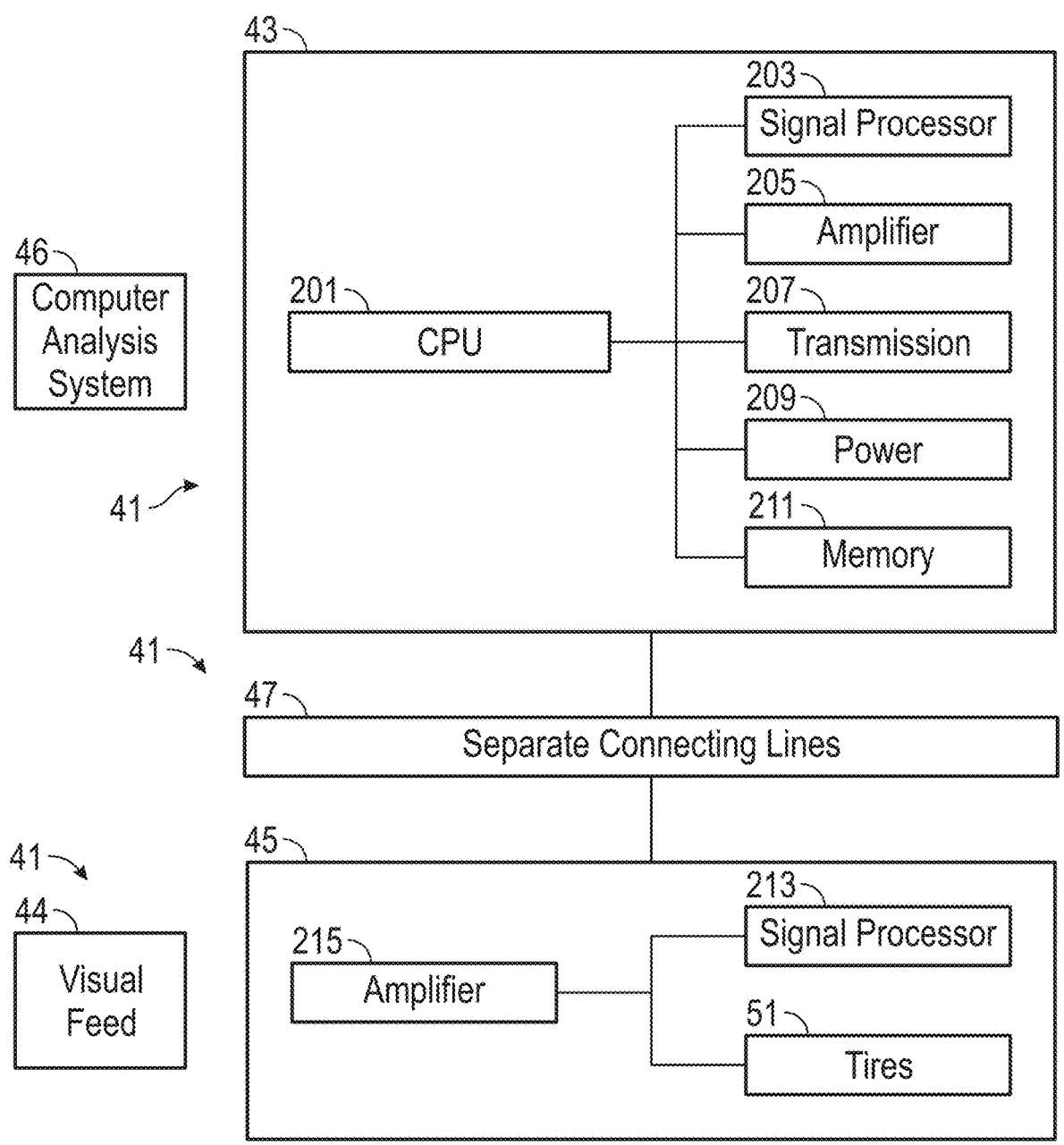
FIG. 2C is a schematic diagram of one embodiment of the electrode assembly and various possible features of the the three components of the electrode array.

The three components of electrode assembly 41 can be wholly passive or alternatively they can contain active electronic devices for various purposes. FIG. 2C is a schematic diagram of electrode assembly 41 and potential various active components. In the embodiment depicted neural modulator 43 has a CPU 201, signal processor 203, amplifier 205, transceiver 207, power supply 209, and memory 211. Electrode array 45 has an amplifier 215, signal processor as well as the tines 51. Ribbon connector 47 has separate connecting lines. Thus, instead of merely being a passive system, the electrode assembly can be an active unit, or remain a passive system that relies on an exterior computer analysis or signal processing system 46. It could take the visual feed from an external video source or other source of a usable signal, process the image, and retransmit it to the target tissue. For example, nerve tissue or similar tissue, when stimulated, generates neural responses. Neural responses tend to be weak signals, but with an amplifier and signal processing capabilities like that in electrode array 41 and neural modulator 45, the system could receive analyze the signals generated by the stimulated tissue and adjust the stimulus signals to be fed in turn to the same tissue. With memory 211 and CPU 201 the system could run various programs to enhance the functioning of the system, and not be dependent on a separate computer analysis system 46 that it needs to connect wirelessly with, which may not always be available. It could process and feed the visual or other signal being sent by the visual signal feed apparatus 44 directly to the target tissue, and adjust the signal feed based on the analysis of the response signals generated by the target tissue.

FIG. 3 is a magnified view of electrode array 45 laid out flat. The embodiment of the electrode array 45 described and depicted herein is made using microfabrication technology, using silicon wafers as the substrate. In the variation depicted, the electrode array has four sections 49A, 49B, 49C, and 49D. Each section has e.g. eight tines 51. As depicted in FIG. 3, the tines of each section have two different lengths, 51A and 51B. In one embodiment, each section 49A, B, C, & D has 16 bonding bumps 53. As will be described below, each bonding bump connects to an electrode in one of the tines 51. Alternatively, the electrode array and the ribbon cable that it connects to, may be fabricated as a single, integrated whole, eliminating the need for bonds to the bonding bumps 53.

Each tine 51 from the point where it connects 55 can be up to 4 mm in length. In the embodiment depicted, each tine is also about five to six microns in diameter or width. FIG. 4 is a substantially magnified view of the end of one of the tines 51. This tine contains two electrodes along its length, 57A and 57B, though additional electrodes can be microfabricated along each tine. The electrodes themselves are the only exposed conductive components of the tine 51; the remainder of the tine is either insulated, or formed from insulating materials. The rest of tine 51 is covered with non-conductive material 59 that is compatible with human tissue and cells. Referring to FIG. 4C tines may be spiked in shape 52A, flat in shape 52D or cylindrical in shape 52C. Also, as depicted in FIG. 4C the electrodes could be flush with the surface of the tine 54A or protrude from the tine 54B. In some embodiments the electrode could protrude from 1 to 30 microns.

Figure 4B:
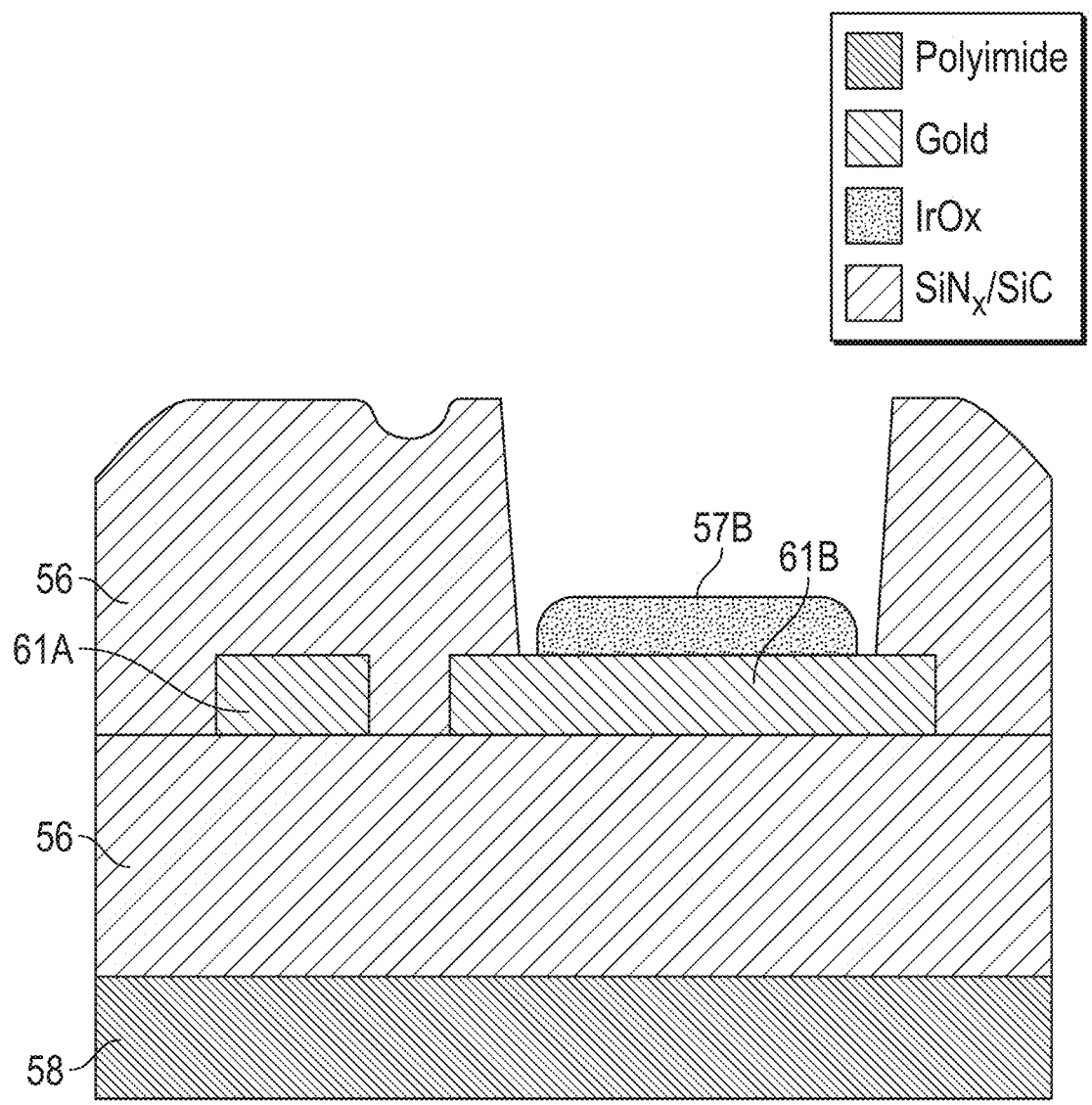
FIG. 4B is a schematic diagram of cross section IV-IV of FIG. 4.
Figure 4C:
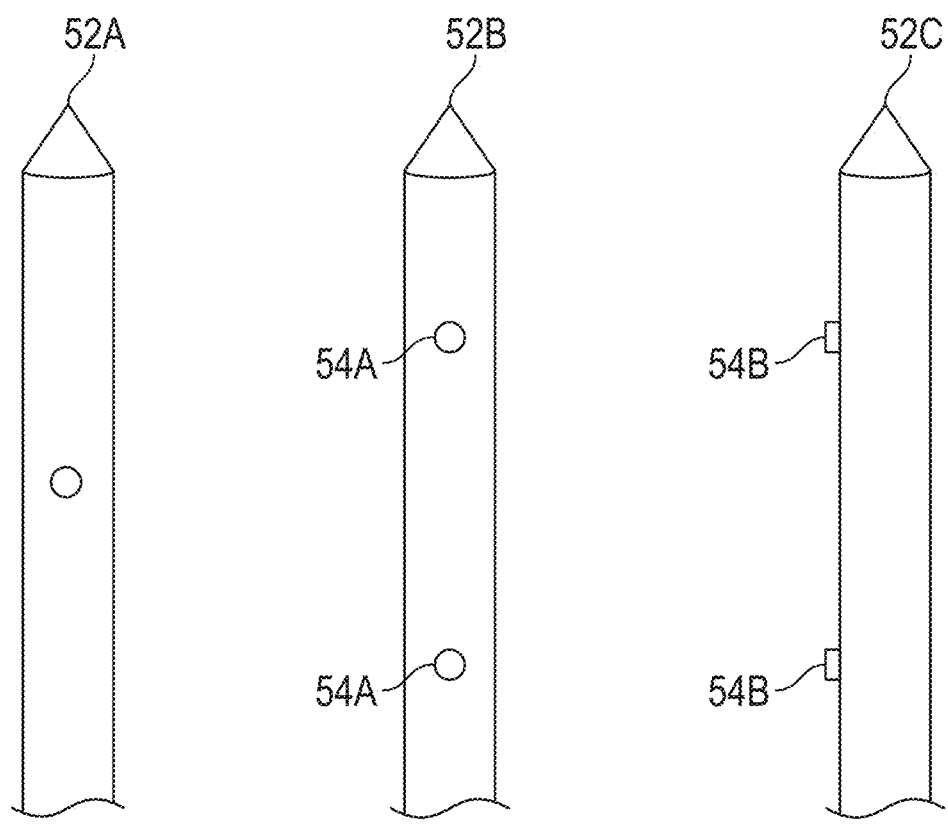
FIG. 4C is a schematic diagram of various potential tine shapes.

FIG. 4A provides a cut away view of tine 51 depicted in filament showing connecting line 61A to electrode 57A and connecting line 61B to electrode 57B, both electrodes are made of iridium oxide (IrOx). FIG. 4B provides a cross sectional schematic view of the tine 51 along line IV-IV of filament. In the embodiment depicted electrode 57B is as noted (IrOx), connecting lines 59A and 59B are gold, insulating layer 56 surrounds and insulates the electrical connection and only leaves the electrodes exposed. In the embodiment depicted the insulating layer is silicon carbide (SiC). Additionally, a layer or polyimide 58 is added for resilience. The micro-fabricated insulating layer 56 can be any suitable inorganic insulating material that provides the necessary rigidity to allow the tines be inserted into the target tissue and at the same time is compatible with the environment of a living organism in particular that can exist for a long time in the environment of a human body. As is well known in the art these materials provide an insulating sealing thin film moisture barrier layer and ion diffusion barrier layer. As is well known the art a polyimide layer may be added as a protective outer coating.

Figure 5:
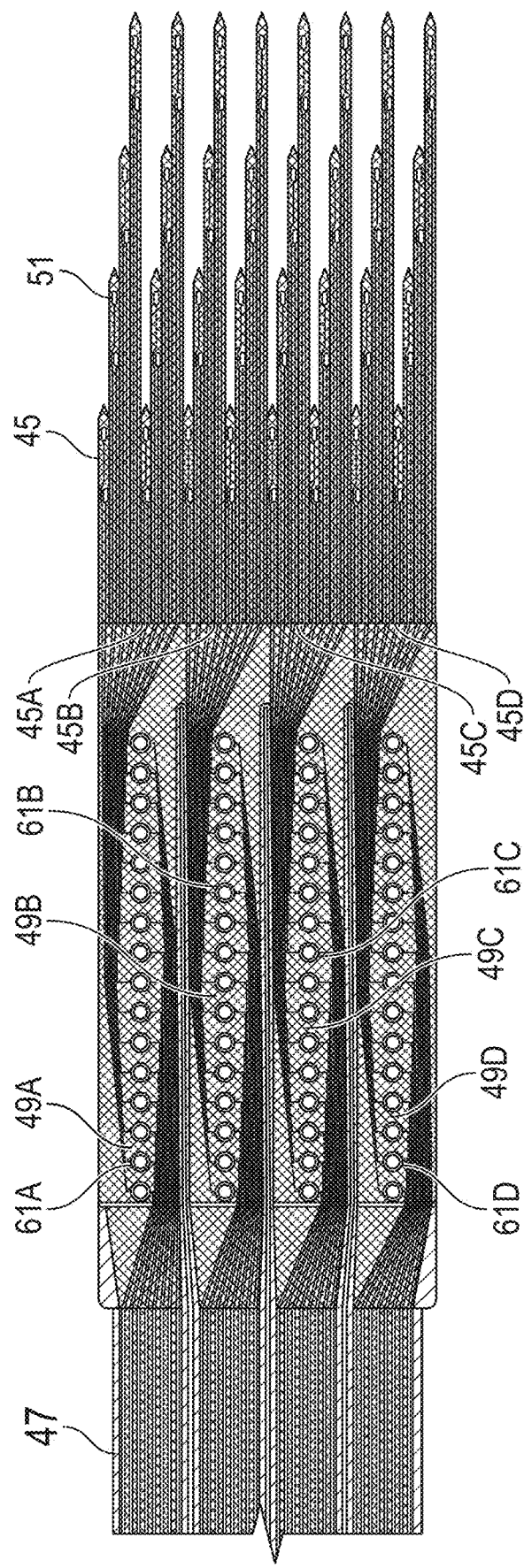
FIG. 5 is schematic diagram of the wiring layout of an embodiment of the electrode array and ribbon connector of the present invention

FIG. 5 is a schematic diagram of the wiring of an embodiment of the invention in which electrode array 45 and ribbon connector 47 are fabricated separately and then connected by connector sections 49A, B, C and D on electrode array 45 to complementary and matched connectors 61A, B, C and D at the proximal end of ribbon connector 47. Further discussion of the connecting bonding pads of this variation will be discussed below. In the variation depicted each section 47A, 47B, 47C and 47D of ribbon connector 47 have sixteen separate communication lines. In turn electrode array has four separate sections 45A, 45B, 45C and 45D. Each section 45A, B, C and D have eight tines with two electrodes on each tine for a total of 64 separate electrodes that connect by their own communication line to stimulator receiver 43 FIGS. 2A and 2B. Thus, in effect the entire structure 45 and 47 FIG. 5 forms a computer bus like structure where each line is capable of sending a separate distinct signal to the electrode connected at the proximal end of the combined structure.

Figure 5A:
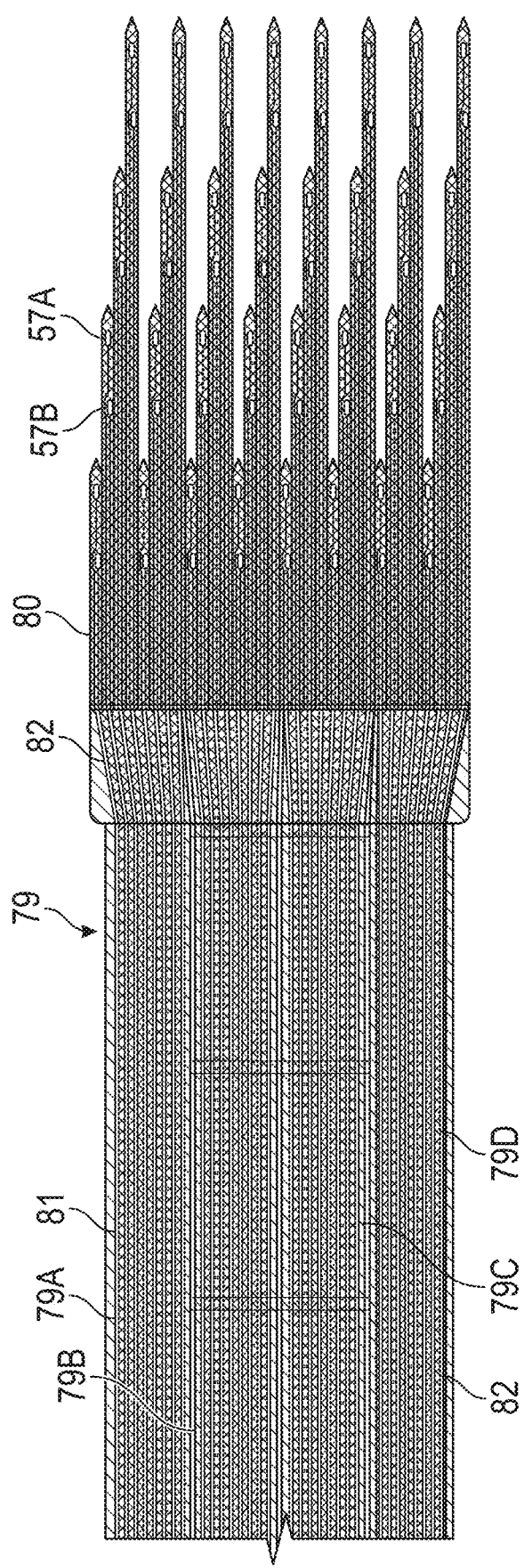
FIG. 5A is a schematic diagram of another variation of the electrode array and ribbon connector which have been fabricated as a single unit.

FIG. 5A is a schematic diagram of a combined electrode array and ribbon connector 79 which have been fabricated as a single unit. This avoids the need for additional connection sections. Combined electrode array-ribbon connector 79 has four separate sections 79A, 79B, 79C and 79D and each of these sections has a total of 16 separate lines for a total of 64 lines. The 64 lines connect to separate electrodes on a total 64 electrodes. There being 8 tines in each of the four separate sections with two electrodes on each tine. Thus, like the variation in FIG. 5 the unitary electrode array-ribbon connector 79 connects the 64 separate electrodes to simulator receiver 43 FIGS. 2A and 2B. The number of lines, tines, electrodes can be varied depending on need or intended use. The variations depicted in FIGS. 5 and 5A are merely meant to be examples of possibilities.

FIG. 6 is schematic diagram of a cross section of an example of five lines that run from the electrode array through the ribbon connector of FIG. 5 or 5A. In FIG. 6 signal conduction lines 82A, B, C, D, and E are made of gold. The signal conduction lines are encased in silicon carbide (SiC) 83. Surrounding SiC layer 83 is a thicker polyimide layer 84 that provides a flexible but resilient covering. The materials cited above are only by way of example other suitable materials could be used for each part. Gold could be replaced with another suitable conductor, and the SIC and polyimide could be replaced with similar inorganic insulating materials that have suitable flexibility, resilience, etc.

FIG. 6A is a schematic diagram of an exposed view of atypical conductive lines 82 in the variation of the electrode array 45 FIG. 3 from a bonding pad 53 to electrode 57 in the tine. In the variation depicted in FIG. 6A insulating material 59 is silicon carbide on a layer of a polyimide 60. As noted above these are just exemplary material. Any suitable material will work that provides the necessary insulation for the conductors, is flexible and resilient. Materials are compatible with living tissue, will not be rejected and which can remain a long time in the living tissue without degrading.

Figure 6B:
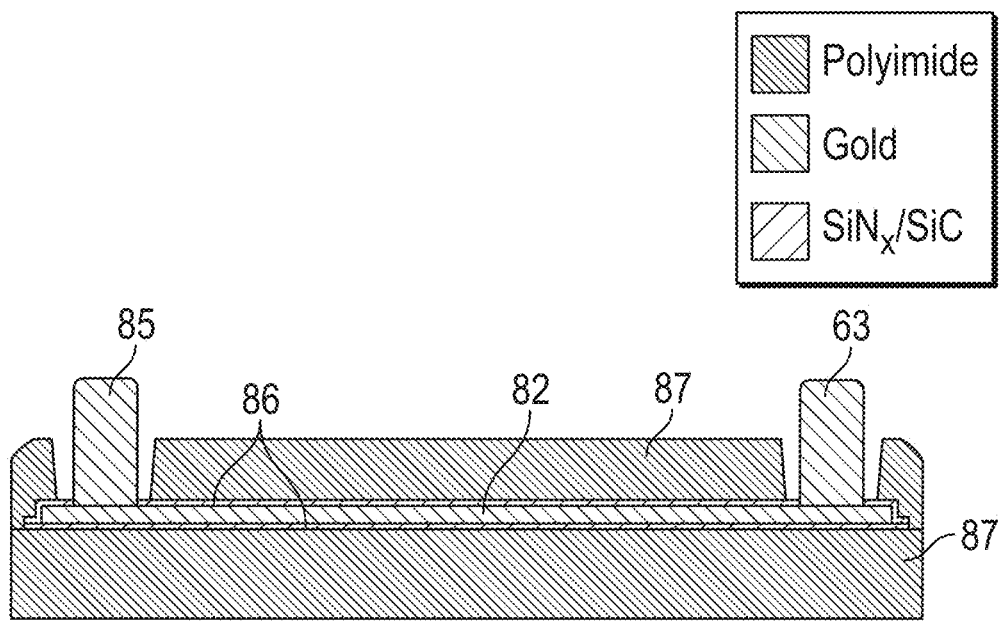
FIG. 6B is a schematic diagram of an exposed view, for illustrative purposes, of a conductive line in a fabricated ribbon connector.

FIG. 6B is a schematic diagram of an exposed view, for illustrative purposes of a typical conductive line 82 in a separately fabricated ribbon connector. Line 82 begins with bonding bumps 63 at proximal end of the ribbon connector. The proximal end being the end that would be joined to a bonding bump on the electrode array. Line 82 ends at bonding bump 85 at the distal end of the ribbon connector. The distal end connects the stimulator, which will be located at the top of the skull. There is a first insulating layer 86, which in the example shown is silicon carbide. Surrounding the first layer 86 is primary insulating and structural layer 87, which in the example depicted is polyimide.

Figure 6C:
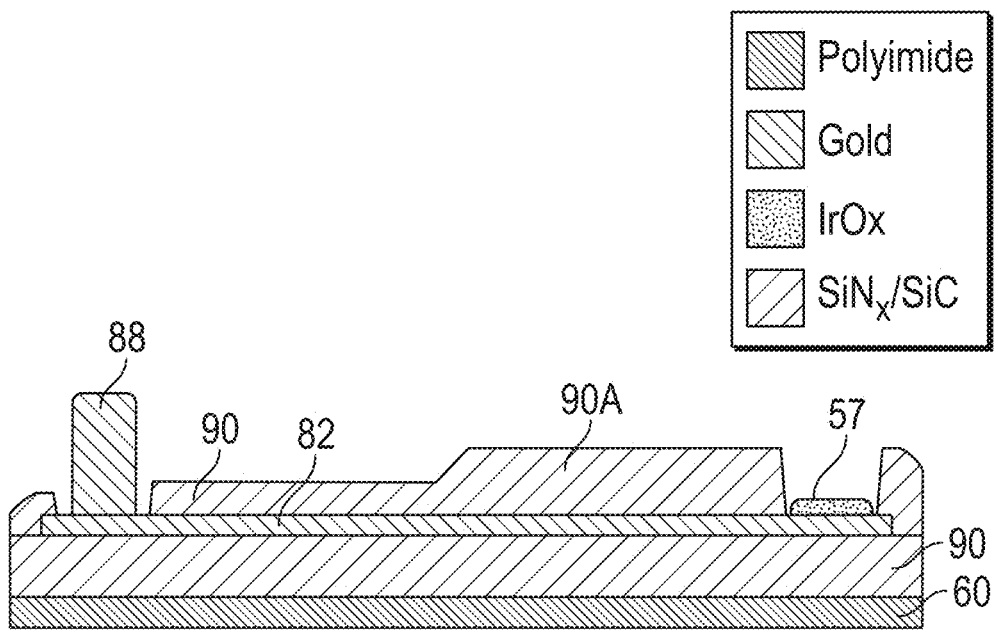
FIG. 6C is a schematic diagram of an exposed line, for illustrative purposes, in an electrode array—ribbon connector fabricated as a unitary structure.

FIG. 6C is a schematic diagram of an expose conductive line, for illustrative purposes, of a conductive line in a unitary electrode array—ribbon connector 79 as depicted in FIG. 5A. Conductive line 82 starts as electrode 57 at the proximal end of the electrode array and runs to bonding bump 88 at the distal end. Bonding bump 88 would connect to the stimulator. In the example shows, insulating structural layer 90 surrounds conductive line 82. The electrode is IrOx, the conductor is gold and the insulating layer is SIC. A polyimide layer 60 is also included. While FIG. 6C represents a passive through-connection between electrode(s) and a neuromodulation device, it is also possible to integrate active electronics on or near the electrode(s) for the purposes e.g. of amplification for recording, or for stimulation.

Figure 7:
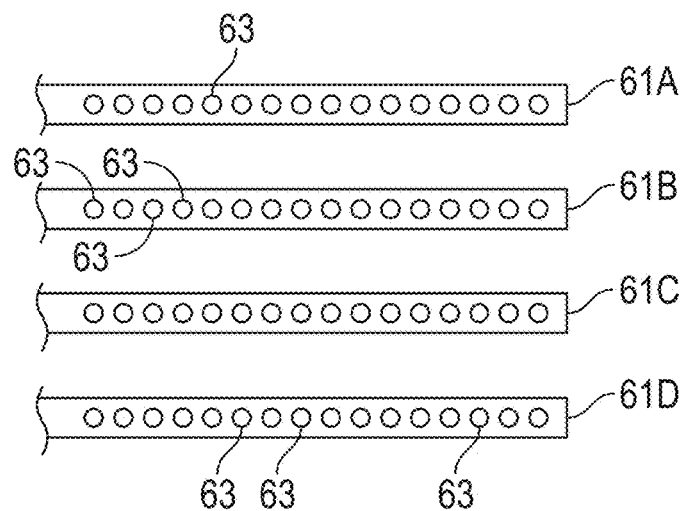
FIG. 7 depicts one possible configuration of the proximal end of the ribbon connector.

FIG. 7 is a magnified view of the connector section 61 at the end of ribbon connector 47. As can be seen, it has four sections 61A, 61B, 61C, and 61D. Each section has 16 bonding bumps 63. These bonding bumps match those on electrode array 45. Sections 61A, 61B, 61C, and 61D connect to the sections 49A, 49B, 49C, and 49D by thermosonic bonding or similar means. It should be noted that in the preferred embodiment of an integrated ribbon cable-electrode array assembly, the connector section of FIG. 7 is not required.

Figure 8:
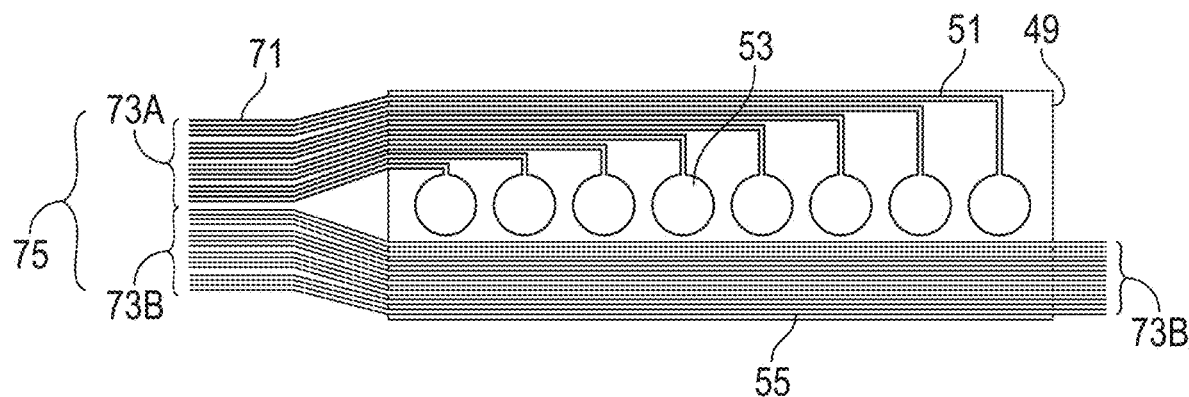
FIG. 8 is a schematic magnified view of a portion of the wiring arrangement of a connector section 49 of the distal end of the electrode array 45.

FIG. 8 is a schematic diagram of the wiring arrangement of a portion of one of the sections of electrode array 45 showing the positioning e.g. of eight of the bonding bumps 53. As can be seen, each of the bonding bumps 53 has a wire 71 that leads to one of the electrodes on one of the tines. As depicted in FIG. 8, eight of the wires 73A run up one side of the section 49, and eight of the wires 73B run up the other side of section 49 and connect to the additional eight bonding bumps on the section 49 which are not shown in FIG. 8. Each of the 16 wires attach to one of the bonding bumps and to one of the electrodes in one of the tines. As with FIG. 7, it should be noted that in the preferred embodiment of an integrated ribbon cable-electrode array assembly, the bonding bumps of FIG. 8 are not required.

Figure 9:
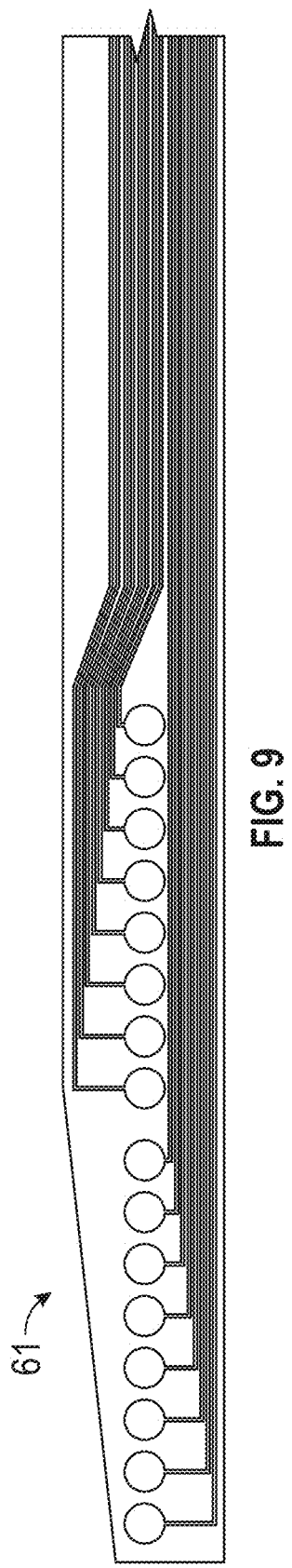
FIG. 9 is a schematic magnified view of a proximal end of a ribbon connector.

FIG. 9 is a magnified schematic view of one of the connector sections 61 of ribbon cable 47. It depicts the wiring arrangement of one of the sections. Each bonding bump 63 on section 61 has its own signal line 77. Each signal line 77 is insulated and runs up the ribbon cable to the implantable stimulator. Thus, since each section of the electrode array has e.g. 16 separate lines and e.g. four sections, so that in this variation, there are a total of 64 separate electrodes in the array. In turn, each electrode has a separate line running up to the implantable stimulator receiver. Thus, in the structure shown, 64 separate signals can be transmitted to different layers of the LGN in four sections. In the embodiment shown, bonding bump 63 and line 77 are made of gold. However, any other suitable conductive material can be used. Thus, as noted above, ribbon cable 47 is similar to a computer 'bus'. Again, it should be noted that in the preferred embodiment of an integrated ribbon cable-electrode array assembly, the connector section of FIG. 9 is also not required.

Thus referring to FIGS. 3 and 7, the connector sections 49 of the electrode array 45 and the connector sections 61 of ribbon cable 47 each have an equal number of bonding bumps 53, electrodes 45, and connection pads 63, and an equivalent number of channels in ribbon cable 47 which can be interconnected by bonding. Thus, when they are connected, they provide an uninterrupted path for signals to run from the implantable stimulator to the electrode(s) on each of the tines. Again, in the case of an integrated ribbon cable and electrode array, these interconnections need not be made; this is a preferred embodiment.

III. Fabrication

As noted above and discussed below the tines, electrode array and ribbon connector are semiconductor structures and fabricated by such fabrication techniques whether they are fabricated as one unit or as a separate ribbon connector and electrode array and them connected. One of the important considerations in fabricating the electrode array and the ribbon connector either as two separate structures that are later joined or as a unitary structure is to minimize stress during the fabrication process. As is well known in the technology of semiconductor fabrication control of stress in laying down the films is achieved by precise control of temperature and pressure, among other parameters. Fabricated parts with too much stress tend to curl or become deformed in other ways, creating issues with the ribbon connector and tines on the electrode array by not having sufficient straightness, etc. Thus, during the micro-fabrication process there is a need to control the net tensile or compressive stress of the material to assure the straightness and proper formation of the tines.

The structures depicted in FIGS. 3 and 9 are fabricated using standard semiconductor fabrication techniques. As noted above, the only electrically active, exposed part of the entire electrode array 45 are the electrode(s) 57 on each of the tines. Electrode(s) 57 are made of iridium oxide, which is sputtered during the fabrication process of the embodiment depicted, although there are other ways to deposit the iridium oxide or other electrode material. Iridium oxide is a preferred embodiment because of its high charge transfer capability between the signal current coming from the stimulator module down the ribbon connector to the electrode array on the one hand, and the target neural tissue on the other hand.

IV. Implant Apparatus

Figure 10:
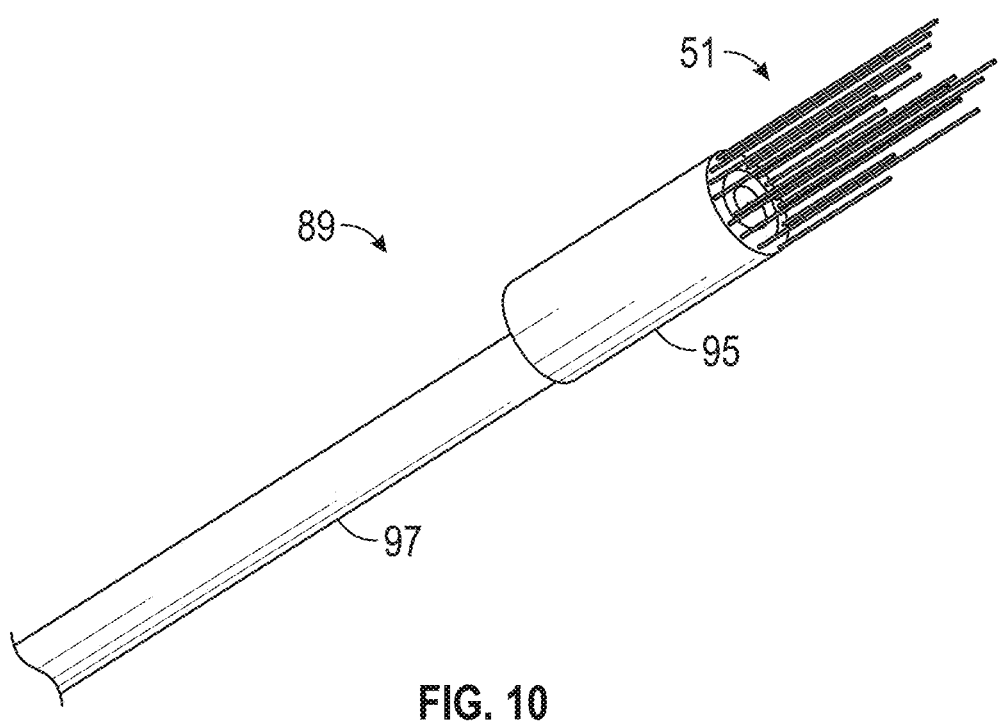
FIG. 10 depicts the electrode array and the end of the ribbon connector rolled up to prepare them for deployment.

The ribbon connector and electrode array, as noted above are very flexible and resilient given the materials they are made from. Also, as noted above when originally fabricated both are flat. In order to prepare the combined ribbon connector and electrode array for deployment during a surgical procedure they need to be rolled into a cylindrical shape for positioning in the split sheath inserter. FIG. 10 provides a magnified schematic perspective view of combined electrode array and ribbon connector 89 rolled up and ready for deployment during a surgical procedure. The lower or distal end of ribbon connector 97 connects to electrode array 95, both of which are rolled up. Tines 51 are visible at the proximal end of rolled up electrode array 95.

Figure 11:
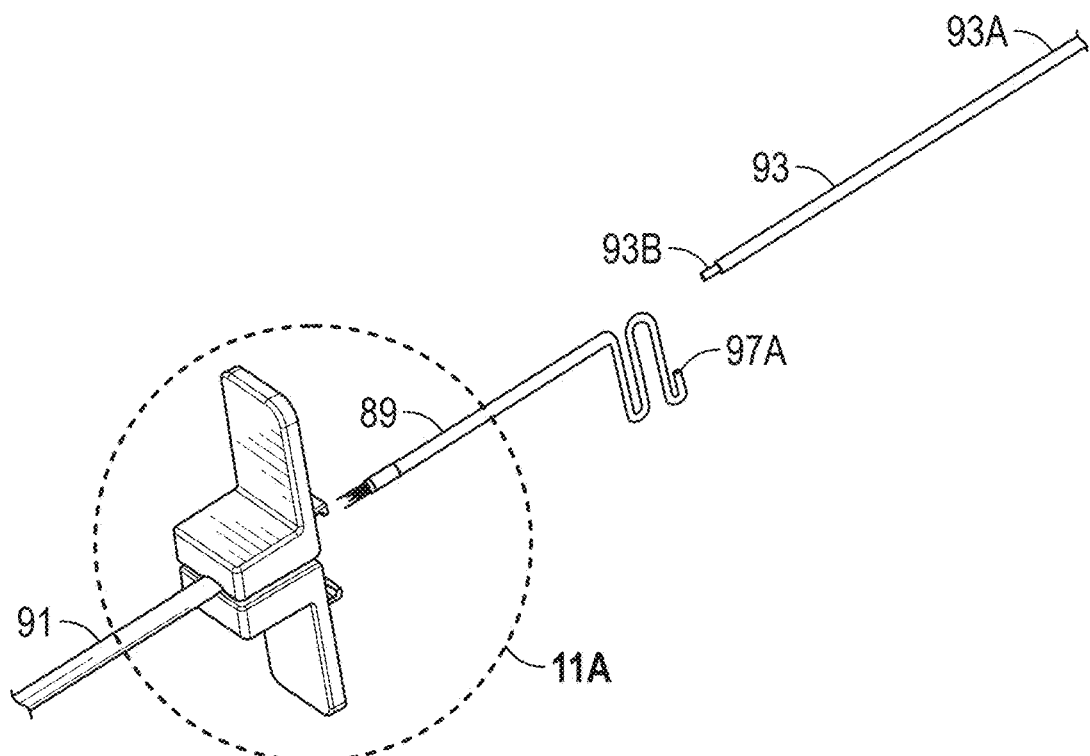
FIG. 11 depicts the fully assembled split sheath inserter, electrode array-ribbon connector and insertion rod ready for assembly together.
Figure 11A:
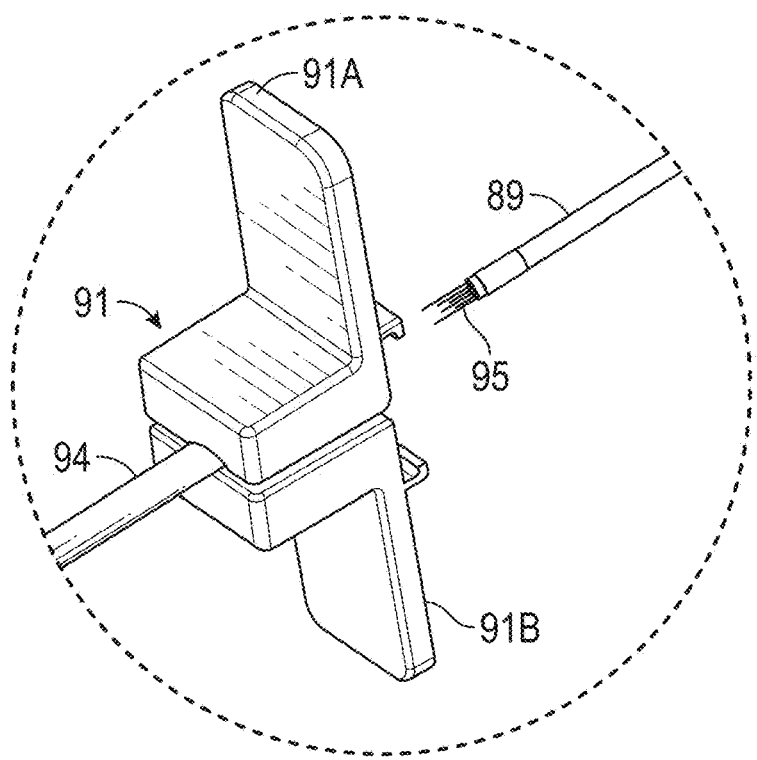
FIG. 11A is cross-sectional cutaway view of FIG. 11.

FIG. 11 depicts the combined rolled up ribbon connector-electrode array 89 with split sheath inserter 91 and advancing or insertion rod 93 all positioned for assembly together. Insertion rod has a proximal end 93A and a smaller distal end 93B. Split sheath inserter 91 with handles 91A and 91B is a standard item used in surgery for providing a channel for the safe and efficient introduction of devices, etc. into a patient that are intended to be placed permanently in the living organism. Once the item which is inserted into the patient implanted in the patient with the split sheath and it is time to remove the split sheath inserter hands 91A and 91B are separated to begin the process of opening up a seam down the split sheath inserter to remove it without disturbing the implanted item. In the present case combined ribbon connector and electrode array 89 will be left in the patient after tines 51 are inserted into the specific tissue that needs to be stimulated. FIG. 11A provides a closer view of the proximal end of combined ribbon connector electrode array 89 and the end of the split sheath inserter that connector electrode array will be inserted into.

Figure 12:
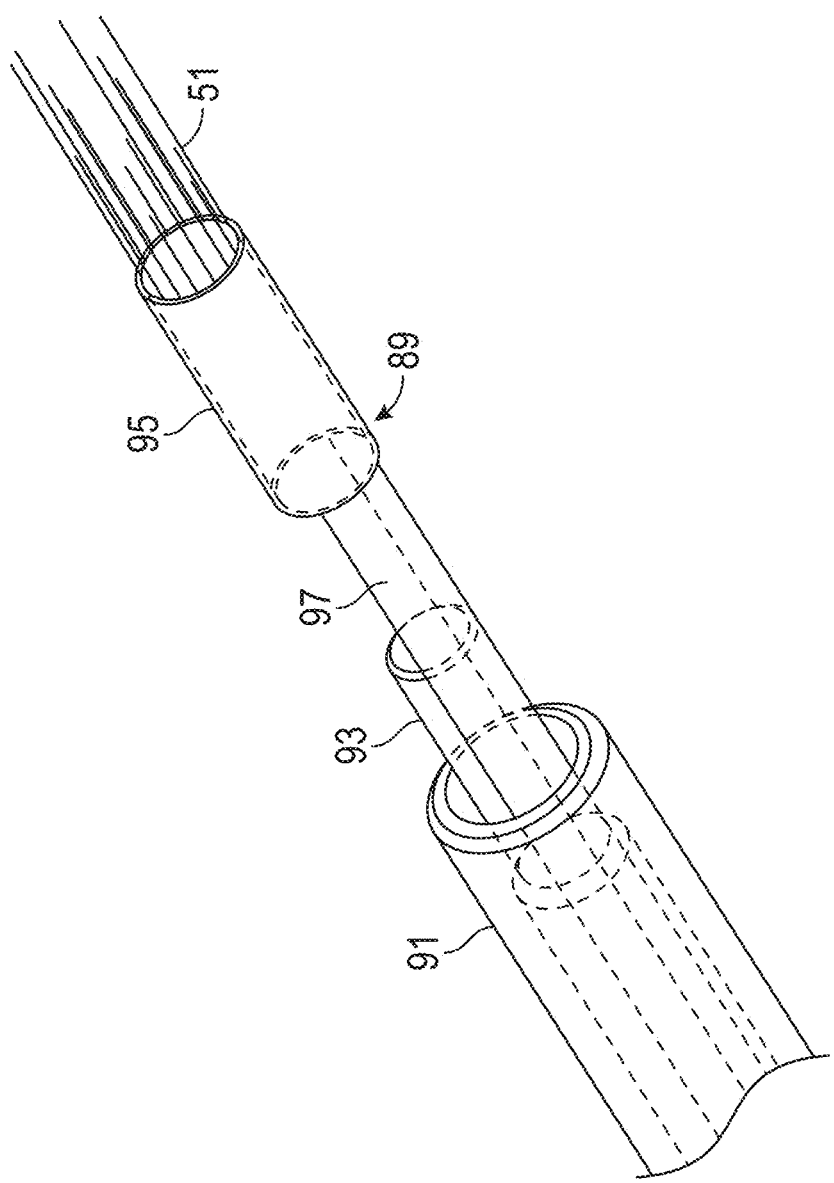
FIG. 12 is an exploded view of the relative position of the split sheath inserter, electrode array-ribbon connector and insertion rod.

FIG. 12 provides an exploded view perspective of the split sheath inserter 91, insertion rod 93 and combined ribbon connector-electrode array 89 with respect to their relative positions during assembly of the three items. FIG. 12 is just provided to show the positional relationship of the items depicted, FIGS. 13 and 13A provide an image of the correct positioning of the items during the initial process of inserting split sheath inserter 91, ribbon connector-electrode array 89 and insertion rod 93. This will be discussed again below during the description of the entire implantation process.

FIG. 13 is a view of split sheath inserter 91 with the rolled up ribbon connector and electrode array 89 and insertion rod 93 positioned inside the split sheath inserter. Just the distal end 97A if ribbon connector 97 is visible sticking out of split sheath inserter with the proximal end of advancing rod 93A. The tines do not stick out of the proximal end 91A of the split sheet inserter 91. FIG. 13A provides a view of the proximal end 91A of split sheath inserter 91 of FIG. 13 at circle 13A with the positon in outline form of electrode array 95 tines 51 and insertion rod 97. As depicted tines 51 of electrode array 95 are wholly recessed in split sheath inserter 91. When the assembly of the split sheath inserter, electrode array-ribbon connector and insertion rod are first inserted into the patient the tines need to be protected until proximal end 91A of the split sheath inserter rests against the LGN. This is to protect the tines which are flexible and somewhat delicate.

Figure 14:
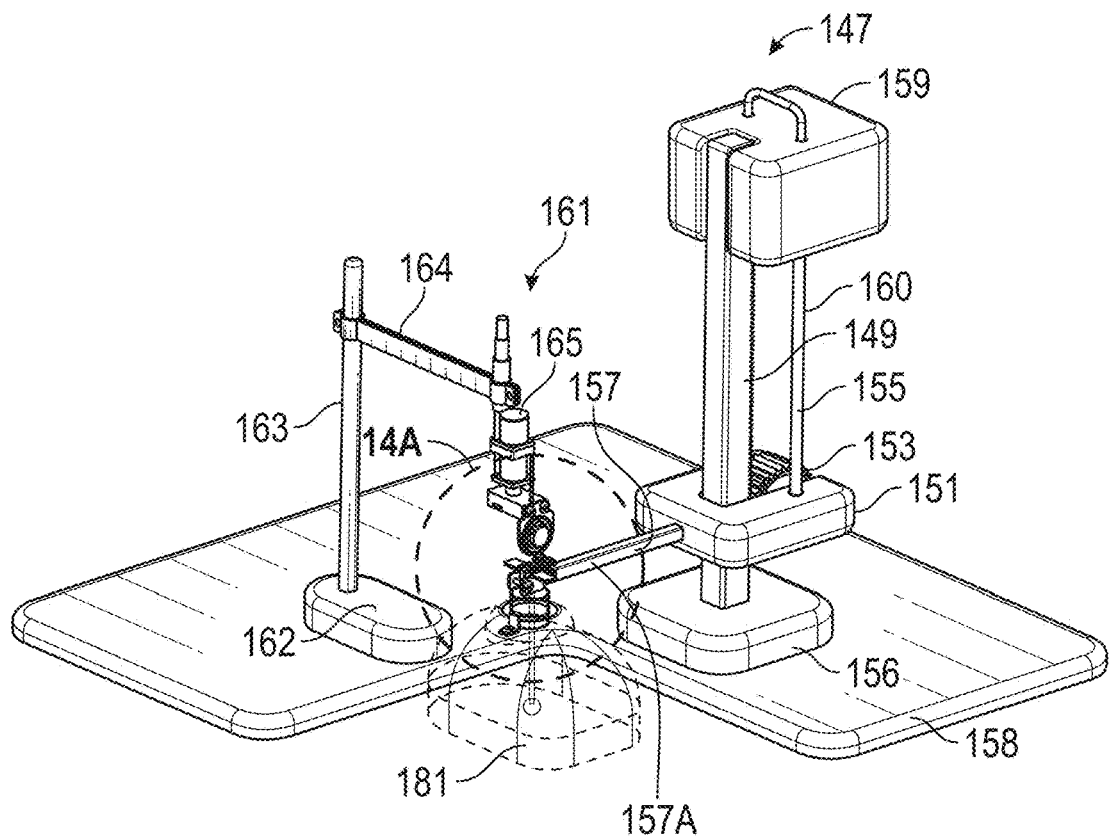
FIG. 14 is a schematic view of the operating mechanisms used to insert the electrode array-ribbon connector into the patient.

FIG. 14 is a schematic diagram of the major operating components used to install the electrode array-ribbon connector. The apparatus depicted consists of a two stage apparatus, a gross positioning instrument 147 and a precision positioning instrument 161. Both are used often in brain surgery and should be familiar to those of ordinary skill in the art. Gross positioning instrument 161 consists of a main shaft 149 on which platform 151 moves up and down by means of gear 153. Arm 157 projects out from platform 151. During the operation end 157A of arm 157 holds the object to be inserted into the patient's brain 181. Shaft 149 attaches to base 156 that attaches to operating table 158. Shaft 149 has a housing 159 at its top which controls movement of platform 151 through control line 160.

Precision positioning instrument 161 has base 162 attached to operating table 158. Support strut 163 attaches to base 162. Support arm 164 attaches to strut 163 and holds precision positioning mechanism 165.

Figure 14A:
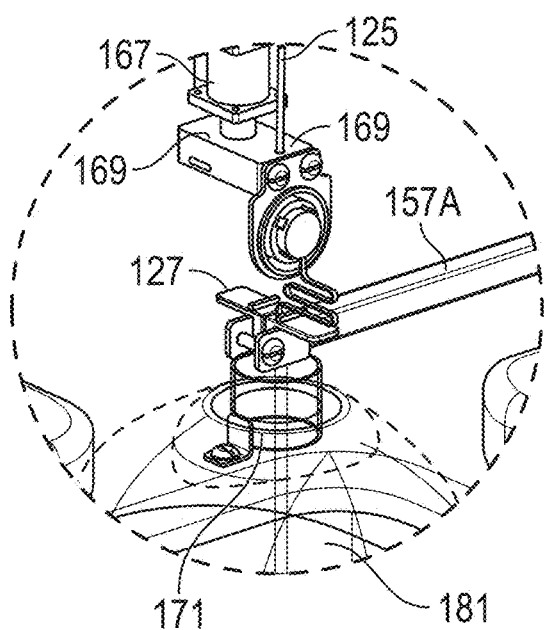
FIG. 14A close up view the precision positioning instrument and advancing portion of the gross positioning instrument above the skull of the patient.

Referring to FIG. 14A precision positioning mechanism 165 includes a hydraulic micro-drive 167 which has a securing bracket 169. Arm 157 has a securing bracket 171. Both securing bracket 171 on arm 157 and securing bracket 169 on hydraulic micro-drive 167 are positioned during the operation over the skull of the patient 181 being operated on.

As depicted in FIGS. 14 and 14A bracket 171 at the end of arm 157 holds split sheath inserter 91 by its handles 91A and 91B. Split sheath inserter holds electrode array-ribbon connector 89 with insertion rod 93. The proximal end of insertion rod sticking out of the end of split sheath inserter. In the initial insertion process gross positioning instrument 147 holding the split sheath inserter and advances the split sheath inserter into the patient's skull 181 after a craniotomy has been completed removing the portion of skull 181 above e the site for insertion. As will be discussed below in more detail once the tip of the split sheath inerter reaches the target tissue or organ, the LGN in the current example, the gross positioning instrument will stop and hold the split sheath inserter in place. Then securing bracket 169 FIG. 14A is attached to the proximal end 93A of inserting or advancing rod 93 and the tines on the electrode array will be inserted into the LGN by hydraulic micro-drive 167. Thus, for fine positioning, the electrode array is pushed with insertion rod slowly into the LGN tissue using a hydraulic micro-drive at –1-5 microns per second. Once this is completed the split sheath inserter will be withdrawn in the standard fashion.

Figure 14B:
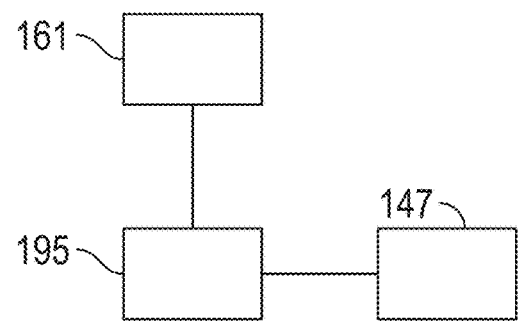
FIG. 14B a schematic of a simple computer aided operating system.

Typically, the physician or physicians performing the procedure will be using a system similar to that depicted in FIG. 14B that uses a computer aided control 195 that controls the function of the gross positioning instrument 147 and the precision instrument 161.

V. Method of Implanting

As depicted in FIG. 1C, the LGN has several layers which deal with different aspects of processing the incoming images for the brain to interpret which enter via the eyes of a human or animal through the LGN. Other CNS tissues may similarly require interaction with tissues at multiple positions and depths. Thus, the varying lengths of the tines 51 of the electrode array 45 are designed to stimulate different layers of the LGN (or other neural tissue, laminated or otherwise, e.g. in a sub-cortical or cortical or other CNS location). Moreover, by controlling the internal stress in the substrate material that the tines 51 are formed from, the angle of deflection from normal incidence to the target tissue (e.g., LGN) can be controlled. This allows the final position of the electrodes 57 and also the stopping position of ends of the tines in space within the target tissue to be planned in advance, resulting in a filled volume of target tissue that has a desired spatial distribution of electrode locations to optimize restored visual outcomes.

Figure 15:
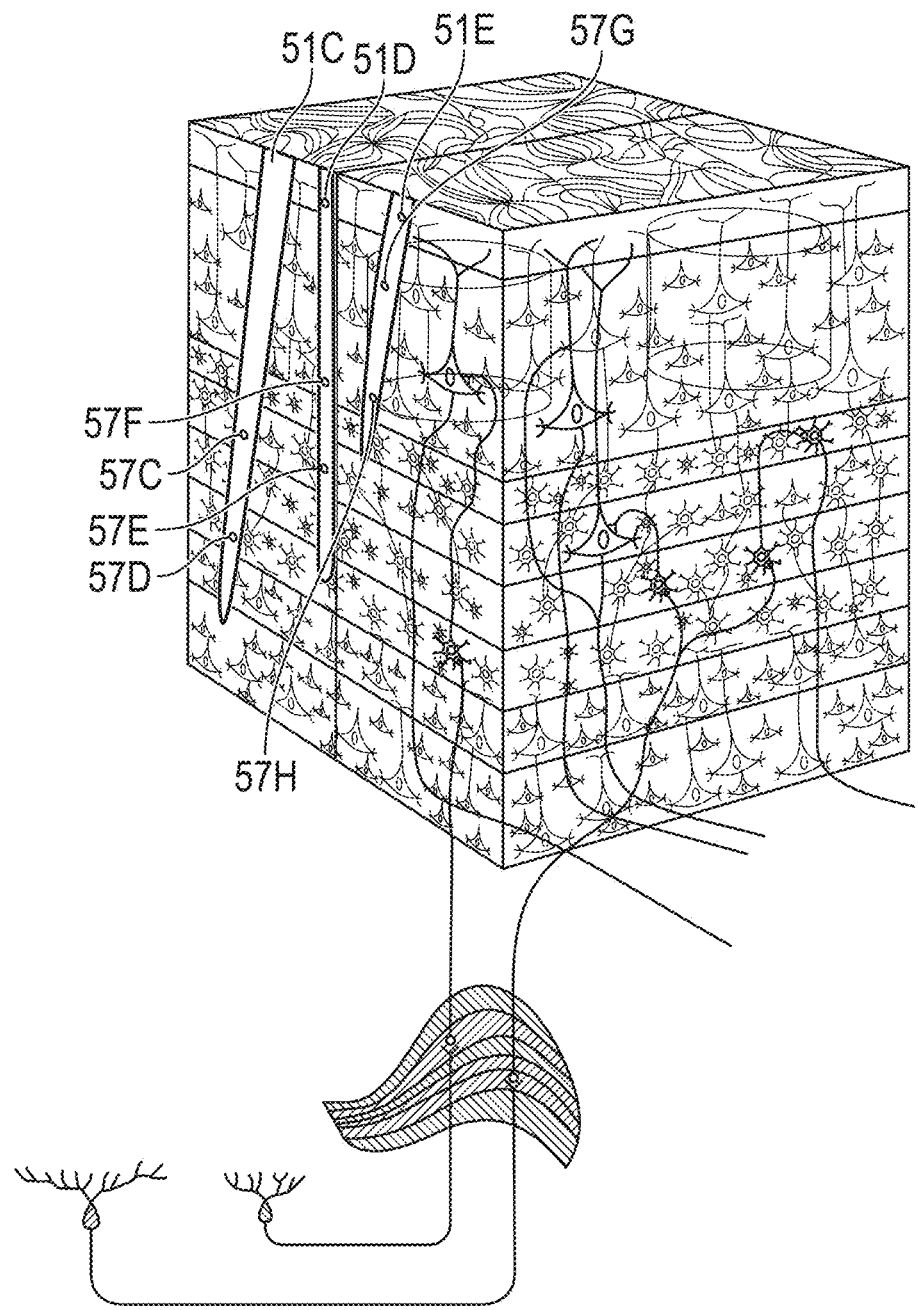
FIG. 15 is a schematic diagram of a small cross section of the LGN that depicts tines penetrating through the layers of the LGN.

FIG. 15 depicts a small cross-sectional schematic diagram of a small area of the layers of the LGN with tines 57 inserted into the LGN using the method and apparatus of insertion described below. As can be seen tines 51C, 51D, and 51E, all of different lengths, have electrodes 57C, 57D, 57E, 57F, 57G, and 57H all positioned to stimulate different layers of the LGN.

FIG. 16 is a flow chart detailing the steps of the implantation process for implanting the electrode array-ribbon connector described above. The first step in the process is to scan the organ in which the implant will be positioned to determine exact location of the target organ or tissue. For the example provided herein this consists of scanning the brain and determining the exact location of the LGN 201. Form the electrode array-ribbon cable assembly into a cylindrical shape and place it inside a split sheath inserter with the distal end of the electrode array with tines completely inside the end of the insert 202. Position an insertion rod in the split sheath inserter with the narrow distal end positioned at the back of the electrode array and the proximal end extending out of the split sheath inserter 203.

Perform a craniotomy in the skull of the subject at a point above the target tissue (e.g., LGN as an example of a deep brain structure, or e.g. a cortical location) into which the electrode array will be inserted 204. Insert the loaded split sheath inserter into the brain coarsely towards the target tissue to the predetermined position on the target organ the LGN 205 using the gross positioning instrument. When the tip of the loaded split sheath inserter reaches the outer edge of the target tissue, stop coarse insertion of the split sheath inserter 206.

Using a hydraulic micro-drive attached to the insertion rod, push the tines of the array slowly out of the split sheath inserter so that it penetrates the target tissue to the desired depth 207. Remove the split sheath inserter in the standard manner by parting the opposing handles of the split sheath inserter 208. Affix the previously-connected packaged stimulator the end of the ribbon cable in the opening previously made in the skull of the patient 209.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A system for modulating neural tissue in a mammal comprising:
   a. an implantable neural modulator;
   b. an electrode array of micro-fabricated ultrathin tines;
   c. a micro-fabricated communication bus with insulated signal lines connecting said set of tines to said neural modulator;
   d. wherein said tines are elongated in shape for insertion into living tissue with an electrically insulated exterior with the exception of at least two electrodes on an exterior of each tine of said tines, said electrodes being individually connected by a separate insulated signal line of said communication bus to said stimulator; and
   e. wherein said set of tines are of varying length so said at least one electrode on each of said tines of said set of tines is positioned at varying depths in tissue as said set of tines are implanted in a target tissue.

2. The system of claim 1 wherein said electrode array and ribbon connector are selected from a group consisting of a ribbon connector and electrode array micro-fabricated as two separate devices and then joined, and a ribbon connector and electrode array micro-fabricated as one unitary device.

3. The system of claim 1 wherein a spatial distribution of said tines in the target tissue is determined by fabrication parameters of said tines, said fabrication parameters being control of a net tensile or compressive stress of the material that the tines are fabricated from during a micro-fabrication process.

4. The system of claim 1 wherein each of at least two electrodes on a tine is at a plurality of electrodes with each said electrode having its own separate insulated signal line in said communication buss.

5. The system of claim 1 wherein a tine of said set of tines can be up to 4 mm long and 2 to 10 microns in diameter.

6. The system of claim 1 wherein the mammal is a human and the target tissue is at least one of the LGN's of the human.

7. The system of claim 6 wherein said neural modulator is placed at the edge of the human's brain and said ribbon connector runs from said neural modulator to said electrode array to thereby communicatively connect them with a source of stimulating signals and also receive neural signals from the LGN.

8. The system of claim 7 wherein said source of stimulating signals is a signal from a camera.

9. The system of claim 1 wherein said shape of said elongated shaped tines is selected from a group consisting tines that are cylindrical in shape, spike shaped, and flat shaped.

10. The system of claim 1 wherein said electrode is configured in a manner selected from a group consisting of an electrode outer surface coplanar with the surface of said tine, and an electrode outer surface projecting out from said tine surface from 1 to 30 microns.

11. The system of claim 1 including signal processor incorporated into to said electrode array to process received signals generated by the target tissue, amplify them and retransmit them to said neural modulator.

12. The system of claim 11 wherein said neural moderator can process and feed the visual or other signal being sent to the target tissue, and adjust the signal feed based on the analysis of the response signals generated by the target tissue.

13. The system of claim 1 wherein said electrode array is a flexible flat planar structure with a first and second surface of said flat planar electrode array covered by a sealing protective layer that provides an insulating sealing thin film moisture barrier layer and ion diffusion barrier layer, and said flexible flat planar electrode array can be configured into a thin narrow shape capable of deep insertion into living tissue prior to deployment of said tines.

14. The system of claim 13 wherein said insulating sealing thin film moisture barrier layer and ion diffusion barrier layer is silicon carbide.

15. The system of claim 13 wherein said thin narrow shape is a cylindrical shape.

16. A method for implanting an electrode array into target brain tissue of a mammal comprising the steps of:
   a. encasing an electrode array with an attached ribbon connector in a split sheath inserter, such that the end of the electrode array with tines is retracted slightly from the front tip of the split sheath inserter and does not extend out of the front end, and the ribbon cable extends out of the back end of the split sheath inserter;
   b. positioning a first end of an insertion rod at a back end of the electrode array and having a second end extending up and out of the end of the split sheath inserter;
   c. Performing a craniotomy in the subject into which the electrode array will be embedded, the hole being cut at a position in the skull to allow insertion of the split sheath inserter to the outside surface of the tissue to be targeted;
   d. positioning the split sheath inserter for insertion into the brain of the subject through the hole cut in the skull;
   e. inserting the split sheath inserter with electrode array, ribbon connector and insertion rod encased in the split sheath inserter at a preset coarse rate until the leading end of the split sheath inserter contacts the outer surface of the target tissue, with navigation guidance e.g. through the brain provided by existing neurosurgical imaging tools;
   f. holding the split sheath inserter still and slowly and precisely inserting the tines at the end of the electrode array into the target tissue by pushing on the back of the electrode array with an insertion rod that is compatible with and connected to existing neurosurgical apparatus (e.g., a hydraulic micro-drive) until the tines are fully embedded in the target tissue, the insertion being informed by recording and monitoring neural activity and/or by stimulating target neural tissue to assess the response, behavior, or perception of the subject;
   g. withdrawing the split sheath inserter and insertion rod; and
   h. positioning the attached stimulator on the skull at the site of the craniotomy.

17. The method of claim 16 wherein the mammal is a human and the target tissue is the LGN.

18. The method of claim 16 further including an initial step of a scanning map of said target tissue prior to the step of inserting the split sheath inserter with electrode array and ribbon connector to thereby precisely locate the position on the target tissue to insert the insert the tines.

19. An electrical connection device for connecting a medical device to living neural tissue comprising:
   a. a ribbon connector with a first end for connecting to a medical device and a tine assembly at a second end for insertion into a target tissue;

b. said tine assembly has a plurality of tines for insertion into the target tissue and each tine of said plurality of tines has an electrically insulated exterior with the exception of at least two electrodes on it's surface, said electrodes being connected by an individual insulated line through said ribbon connector to said first end of said ribbon connector, wherein said insulated exterior is an insulating sealing thin film moisture barrier layer and ion diffusion barrier layer;

c. said plurality of tines are of different lengths to thereby place said at least one electrode on each of said tine of said plurality of tines at different depths of the target tissue; and d. wherein each individual electrode with said individual insulated line can transmit a separate signal or receive a separate signal from the target tissue.

20. The electrical connection device of claim 19 wherein a neural modulator can be connected to said first end of said electrical connection device and thereby transmit or receive signals on each of said individual insulated line of each of said electrodes to the target tissue.

21. The electrical connection device of claim 19 wherein said at least two electrodes on said tine is a plurality of electrodes on said tine, each electrode having a separate insulated line to said connector at said first end.

22. The electrical connection device of claim 19 wherein said at least two electrodes on said tine is a plurality of electrodes on said tine, and wherein at least two electrodes of said plurality of electrodes share an insulated line to said first end of said ribbon connector.

23. The electrical connection device of claim 19 wherein said tine assembly includes signal processing circuits to process signals received by said electrode from the target tissue for transmission to said first end of said ribbon connector for reception by a medical device attached to said first end.

24. The electrical connection device of claim 23 wherein said neural modulator processes signals received from the target tissue to adjust the signal it then transmits to the target tissue over said connected insulated lines of said tines.

25. The electrical connecting device of claim 19 wherein said ribbon connector is a flexible thin flat planar structure covered on a first and second side by a sealing layer and said ribbon connector can be rolled into a thin narrow shape for deep insertion in to living tissue prior to deployment of said tines in target tissue.

26. The electrical connecting device of claim 19 wherein said insulating sealing thin film moisture barrier and ion diffusion barrier layer is silicon carbide.

\* \* \* \* \*